(12) United States Patent  (10) Patent No.: US 7,821,248 B2
Reymond et al.  (45) Date of Patent: Oct. 26, 2010

(54) DEVICE AND METHOD FOR COUNTING ELEMENTARY PARTICLES EMITTED BY A FLUID IN A CONDUIT

(75) Inventors: Jean-Marc Reymond, Saint-Remy-les-Chevreuse (FR); Sophie Kerhoas-Cavata, Raizeux (FR); Philippe Mangeot, Le Kremlin-Bicetre (FR)

(73) Assignee: Commissariat A l'Energie Atomique, Paris (FR)

( * ) Notice: Subject to any disclaimer, the term of this patent is extended or adjusted under 35 U.S.C. 154(b) by 123 days.

(21) Appl. No.: 11/963,156

(22) Filed: Dec. 21, 2007

(65) Prior Publication Data

US 2008/0315860 A1  Dec. 25, 2008

(30) Foreign Application Priority Data

Jun. 19, 2007 (FR) .................................. 07 04348

(51) Int. Cl.
G01N 15/00 (2006.01)
G01N 33/48 (2006.01)
(52) U.S. Cl. ....................... 324/71.4; 250/222.2; 356/39
(58) Field of Classification Search ................ 324/71.4; 250/222.2; 356/441
See application file for complete search history.

(56) References Cited

U.S. PATENT DOCUMENTS

| 3,811,841 | A | * | 5/1974 | Kassel ........................... 422/82 |
| 3,864,551 | A | * | 2/1975 | Oefinger ........................ 377/12 |
| 4,412,004 | A | * | 10/1983 | Ornstein et al. ................ 436/10 |
| 4,979,824 | A | * | 12/1990 | Mathies et al. ................ 356/318 |
| 5,690,895 | A | * | 11/1997 | Matsumoto et al. ............ 422/73 |
| 6,136,171 | A | * | 10/2000 | Frazier et al. ................. 204/450 |
| 6,169,394 | B1 | * | 1/2001 | Frazier et al. ................ 324/71.4 |
| 6,703,819 | B2 | * | 3/2004 | Gascoyne et al. ............ 324/71.4 |
| 6,794,671 | B2 | * | 9/2004 | Nicoli et al. ................. 250/574 |
| 2005/0167583 | A1 | * | 8/2005 | Miller et al. ................. 250/290 |
| 2006/0085020 | A1 | | 4/2006 | Freeman |
| 2007/0010974 | A1 | * | 1/2007 | Nicoli et al. ................. 702/196 |
| 2007/0083160 | A1 | | 4/2007 | Hall et al. |

FOREIGN PATENT DOCUMENTS

WO WO 03/003923 1/2003
WO WO 2007/093913 8/2007

OTHER PUBLICATIONS

Search Report from priority document French Patent No. 07/04348, filed Jun. 19, 2007.

* cited by examiner

*Primary Examiner*—Timothy J Dole
*Assistant Examiner*—John Zhu
(74) *Attorney, Agent, or Firm*—Alston & Bird LLP

(57) ABSTRACT

The invention relates to a device and a method for counting elementary particles emitted by a fluid, the device comprising a line for transferring the fluid and, outside the line, detection means (6a) for detecting the particles that are attenuated by a wall of the line and/or by this fluid.

A counting device according to the invention includes at least one counting portion (4a) of oblong cross section which joins together two adjacent portions of the line having a larger flow section and which has an [internal height (h)/internal width (l)] ratio of 20% or less, in which the internal height and the internal width represent the smallest and largest transverse dimensions respectively of the portion, these being measured along two approximately perpendicular directions, said detection means extending transversely to this portion, facing its entire internal width and on either side thereof.

18 Claims, 2 Drawing Sheets

DEVICE AND METHOD FOR COUNTING ELEMENTARY PARTICLES EMITTED BY A FLUID IN A CONDUIT

FIELD AND BACKGROUND OF THE INVENTION

The present invention relates to a device and a method for counting elementary particles (such as α-particles, γ-particles, electrons or positrons) emitted by a fluid, the device having a line for transferring this fluid and, outside the line, means for detecting these particles that are attenuated by a wall of the line and/or by this fluid. The invention applies more particularly, but not exclusively, to a fluid consisting of blood microsamples taken from a mammal.

As is known, the counting of particles attenuated by certain components of a fluid that incorporates them and/or by the wall of the line transferring this fluid poses certain technical problems, which are particularly acute in the particular case of counting within small fluid samples, in the case of absorption of these particles by the fluid, or else in the case when the particles to be counted are electrons or positrons emitted by beta-radioactivity in particular. Among these applications in which these three problems are combined, mention may mainly be made of those for direct measurement of the positrons or electrons coming from the beta-radioactivity contained in blood microsamples, for example for devices for measuring the entry function of a mammal intended for quantitative imaging.

A number of laboratories, such as that at Sherbrooke in Canada, have developed positron or electron detectors for blood microsamples incorporating beta-emitters as radiotracers, by providing counting devices, the detector efficiency of which does not exceed 7% in the case of $^{18}$F radiotracers and 16% in the case of $^{11}$C radiotracers. These devices include a tubular line of constant flow section over its entire length, without any particular feature in its detection zone provided with the detectors. This line has an internal diameter of 0.58 mm and since the mean free path of positrons in blood is about 0.6 mm in the case of $^{18}$F, it follows that few positrons emerge from these blood microsamples. In addition, the material used for this line—a low-density polyethylene (LDPE)—since it has a very large wall thickness e (e≧150 μm and typically equal to 192.5 μm) for a density d close to 1 g/cm$^3$ (typically equal to 0.92 g/cm$^3$ in the case of "PE10"), it follows that this line results in a relatively high attenuation of the electrons or positrons, this being proportional, as is known, to the product exd, which here is typically equal to 192.5×0.92, i.e. about 177.

Also known, by the name "β-microprobe", are other particle counting methods and devices that are used by the French company Biospace for measuring the entry function of a small mammal, such as a rat or a mouse. These methods essentially consist in eliminating the aforementioned line, introducing the detector directly into an artery of the animal, in the state immersed in the blood of the latter.

One major drawback of this lineless solution is that the radiotracer accumulated in the other organs of the animal creates a strong perturbation by gamma-radiation. Another drawback of this solution lies in the small dimensions characterizing the measurement, which leads to a low counting efficiency. It is therefore necessary to add a second detector to the main detector, the second detector being placed in the body of the animal but not in its blood, and a differential procedure is used to subtract the background noise due to this gamma-radiation.

Even under these measurement conditions, it turns out that the stated detection efficiency (which is reduced by absorption in the blood) is only 16% and 20% in the case of radiotracers based on $^{18}$F and $^{11}$C, respectively, using a scintillating plastic detector 1 mm in diameter.

Given the recent developments in technologies for treating microsamples and the desire of biologists to develop tools intended for small animals, such as mice, it is of fundamental importance to be able to measure the activity of liquid microsamples containing the least possible amount of radiotracers. Since these microsamples have a volume of the order of a few μl (typically 8 to 30 μl), it is necessary for the counting devices used to have a high efficiency (i.e. a high measurement sensitivity), particularly for studying short-lived radiotracers such as $^{11}$C, the activity of which at the end of a sequence decreases significantly (the half-life of $^{11}$C being 20 minutes).

SUMMARY OF THE INVENTION

The object of the present invention is to propose a device for counting elementary particles emitted by a fluid, the device comprising a line for transferring this fluid and, placed outside said line, detection means for detecting these particles, said particles being attenuated by a wall of said line and/or by this fluid, which device remedies the aforementioned drawbacks by having an improved measurement sensitivity.

For this purpose, a counting device according to the invention is such that it includes at least one counting portion of oblong cross section which joins together two adjacent portions of this line having a larger flow section and which has an [internal height/internal width] ratio of 20% or less, in which the internal height and the internal width represent the smallest and largest transverse dimensions respectively of the portion, these being measured along two approximately perpendicular directions, said detection means extending transversely to this portion, facing its entire internal width and on either side thereof.

It will be noted that if the particles to be counted are electrons or positrons, this extremely flattened geometry of the counting portion combined with its relatively high internal width, said detection means being arranged so as to face said width and overhang it, gives a very high counting efficiency, typically greater than 50% both for $^{18}$F and $^{11}$C radiotracers, thus making measurements possible even on blood microsamples having a volume of less than 10 μl (typically those taken from mice) and possibly containing short-lived radiotracers (such as $^{11}$C).

In particular, it should be noted that this arrangement of said detection means, both facing and overhanging the transverse width of the counting portion makes it possible to maximize the geometric acceptance of these detection means (i.e. to maximize all the directions in space in which a radiotracer molecule may emit an elementary particle whose path impacts the detection means, making its "capture" possible), thus contributing to proving this counting efficiency.

The term "flow section" is understood in the present description to mean the internal cross section of the counting portion (of oblong or flattened shape) and that of each of the two (preferably circular) portions adjacent this counting portion.

When the fluid is a liquid, this counting portion preferably has an [internal height/internal width] ratio of between 5% and 10%.

Advantageously, the ratio of the flow section of the counting portion to that of each adjacent portion may be equal to or less than 35%, and even more advantageously less than 25%.

Also advantageously, said internal height of the counting portion may be less than 20% of the internal diameter of each of the adjacent cylindrical portions and said internal width of this portion is greater than 1.3 times this internal diameter.

According to a preferred embodiment of the invention, this counting portion has an approximately rectangular cross section, the long sides and/or the short sides of which are curved with mutually symmetrical curvatures, so that this portion has at least partly a substantially convex or concave external face.

According to another preferred feature of the invention, said line is designed for the flow of liquid microsamples, such as blood microsamples, said internal height of the counting portion being between 100 μm and 250 μm and said internal width of this portion being greater than 1.3 mm, whereas the or each adjacent cylindrical portion has a diameter of between 0.8 and 1.2 mm.

The term "microsamples" will be understood in the present description to mean liquid samples each having a volume of less than 100 μl, and preferably equal to or less than 30 μl (i.e. typically samples taken from small animals).

Even more preferably, the area of the flow section of said counting portion is between 0.15 mm² and 0.25 mm² and this portion has a length of between 30 mm and 40 mm so as to be able to contain a microsample of about 8 μl facing said detection means.

Specifically when the particles to be counted are electrons or positrons resulting from the beta-radioactivity emitted by said fluid, said counting portion advantageously has a wall thickness e, expressed in μm, and a density d, expressed in $g/cm^3$, the product e×d of which is less than 100 and preferably less than 50, in such a way that the attenuation by this portion of particles to be counted is minimized.

According to another advantageous feature of the invention, which relates in particular to such particles of the electron or positron type, said counting portion is based on a thermoformed polymer with a density of 1.5 $g/cm^3$ or less, preferably a polyimide of the "Kapton" brand, and this portion has a wall thickness of less than 50 μm and preferably less than 30 μm. Preferably, this material is chosen to be biocompatible if the measured liquid is a biological fluid and capable of being reinjected into a living being.

It will be noted that this selection of such a "Kapton"-type polyimide makes it possible to obtain this very low value of the aforementioned product e×d, compared with the usual values of this product, which are generally between 150 and 200 in the case of the known lines made of LDPE, which have a lower density than that of this "Kapton" polyimide but have a very substantially greater thickness.

According to another feature of the invention, said detection means advantageously comprise two sets of detectors placed respectively against or in the immediate vicinity of two approximately plane large faces of said counting portion, which faces are separated from each other by said height and are joined together by two small faces of this portion, these sets of detectors overhanging said small faces in the direction of said width in order to maximize the geometric acceptance of said detectors.

According to one particular embodiment of the invention, said device may be placed upstream of a computer-controlled peristaltic pump for sucking up, in bursts, a specified amount of samples to be taken, said large faces of said counting portion each having an advantageously slightly convex shape on their external side.

It should be noted that this convex geometry of the large external faces of the counting portion is advantageously usable in general when the fluid flowing in the line is subjected to a pressure surge or to a pressure that varies over time, for example in the case of samples being taken in successive suction operations.

The elementary particle counting method according to the invention is implemented by means of a counting device as defined above, and this method consists in particular in choosing for the wall of said counting portion a material that is substantially transparent to the particles emitted by said fluid.

According to a first exemplary embodiment of the invention, the particles are photons emitted by fluorescence and in this case the wall of this portion must be chosen to be transparent at the wavelength of the photons in question.

According to a second exemplary embodiment of the invention, the particles are electrons or positrons emitted by beta-radioactivity, said wall having a thickness e, expressed in μm, and a density d, expressed in $g/cm^3$, such that the product e×d is less than 100 and preferably less than 50, so as to minimize the absorption of these particles so as not to significantly affect the counting.

Advantageously, this counting method according to the invention is such that said fluid consists of blood microsamples that flow in said line, and in the plasma of which microsamples a short-lived beta-radiotracer, such as carbon 11, is diluted.

Even more advantageously according to this method of the invention, said microsamples have been taken in succession from a mammal, such as a rat or a mouse, and each has a volume of less than 100 μl and preferably equal to 30 μl or less, the entire volume of each microsample being substantially located within said counting portion facing said detection means, so that these microsamples follow one another in this portion as discrete packets both in space and in time.

It will be noted that the small size of the animals that are preferably used for the measurement on the microsamples taken requires the total volume of these microsamples to be limited to an amount that is compatible not only with the health of the animal, but also with its metabolism being as disturbed as little as possible.

BRIEF DESCRIPTION OF THE DRAWINGS

The above features of the present invention, together with others, will be more clearly understood on reading the following description of several exemplary embodiments of the invention, given by way of nonlimiting illustration, said description referring to the appended drawings in which.

DETAILED DESCRIPTION

Figure 1:
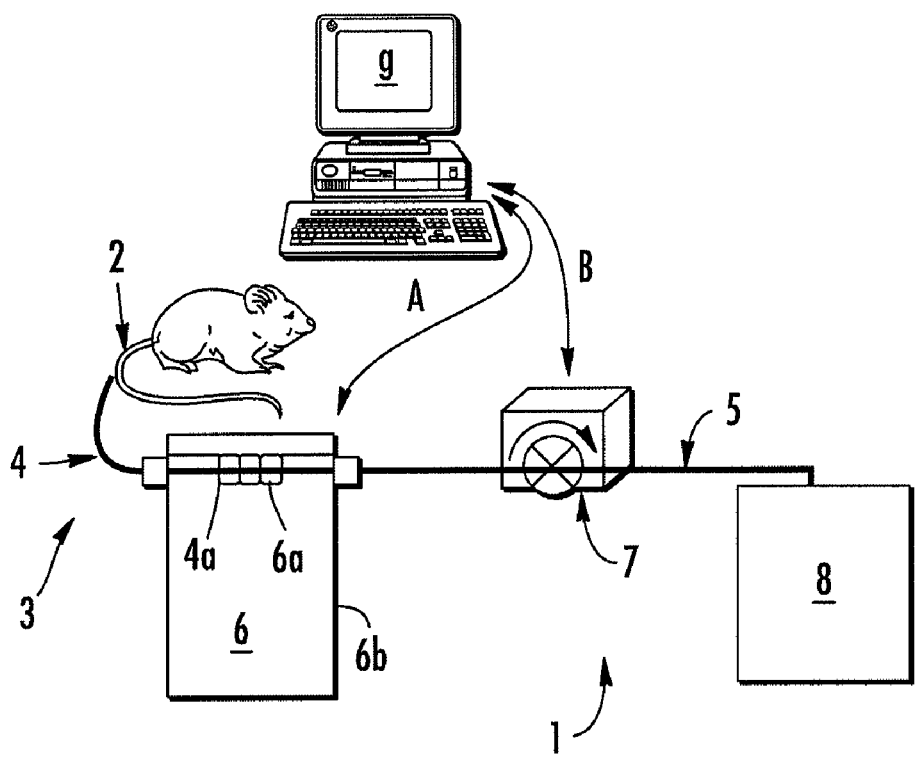
FIG. 1 is a schematic partial view of an automated sampling and measurement system according to the invention, including a radioactivity, for example a beta-radioactivity, counting device placed upstream of a sample treatment device for treatment of the microsamples taken.

FIG. 1 illustrates by way of example an automated installation 1 for carrying out, in succession and continuously, the taking of blood microsamples from a small mammal 2, for example of the rat or mouse type, for temporarily storing said microsamples and for carrying out radioactive measurements thereon, by means of a sampling system 3 that includes a succession of lines 4 and 5 of the flexible capillary or microtube type. This sampling system 3 essentially comprises:

- a catheter which is equipped with a connection device (not illustrated) and is intended for sucking up, in bursts, the same amount of blood to be taken, via a peristaltic pump 7;
- a counting device 6 for counting the particles present in the microsamples taken, which in this example is a counter 6 that counts positrons or electrons resulting from the beta-radioactivity for total blood microsamples and which is placed as close as possible to the sampling point, being virtually in contact with a counting portion 4a of this succession of lines 4, 5 (as explained below, this portion 4a has shape and material characteristics that are optimized for this counting and is centered with respect to the detection diodes 6a that the counter 6 comprises);
- a sample treatment system 8 placed downstream of the peristaltic pump 7, where these microsamples taken and analyzed are stored and treated; and
- a computer-aided control device 9 for controlling the entire system 3, including this pump 7 (see the double arrows A and B in FIG. 1 for this control).

According to the invention, the succession of lines 4 and 5 is advantageously such that the enlargements in their cross section present along these lines are always less than or equal to 20% in terms of area ratios so that the microsamples following one another in this succession of lines 4 and 5 undergo practically no mixing therein by diffusion. In this way, these microsamples taken are in discrete packets both in space and in time.

Figure 2:
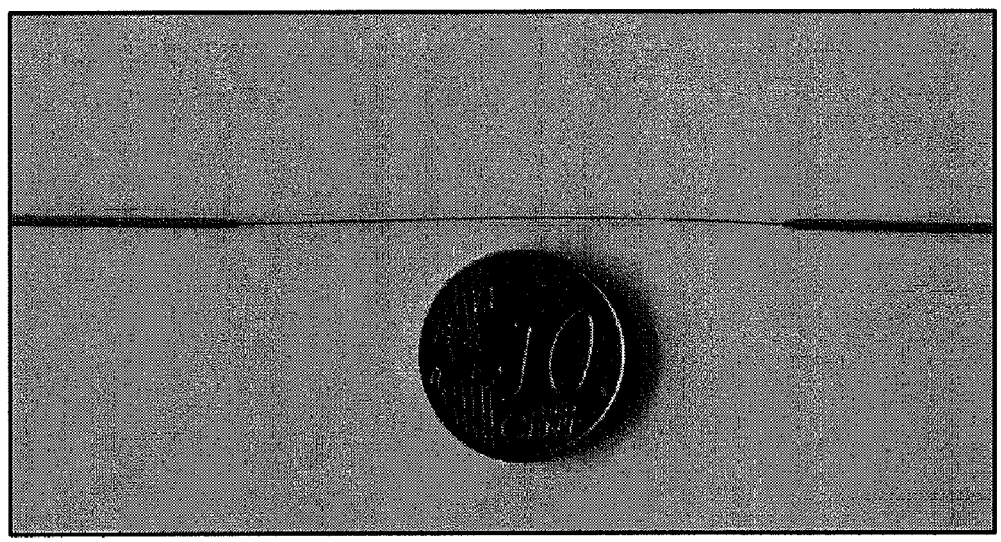
FIG. 2 is a photograph illustrating the shape and relative dimensions, in comparison with a euro 10-cent piece, of a line of this sampling and measurement system including a flattened portion which is capable of optimizing this radioactivity counting.
Figure 3:
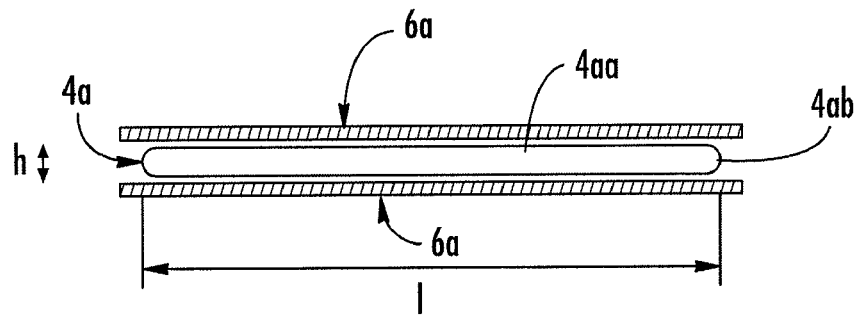
FIG. 3 is a schematic view in cross section of this flattened portion according to the invention, equipped with two sets of detectors illustrated in FIG. 1.

As illustrated in FIGS. 2 and 3, a flattened counting portion 4a is provided in the succession of sampling lines 4, 5 according to the invention, which flattened portion joins together two cylindrical portions and is designed to optimize the particle counting by the device 6 of FIG. 1 (such as the beta counter, advantageously used for measuring the entry function of the small mammal 2). In this way, the detection volume chosen is reduced and the counting efficiency is increased.

For this purpose, said flattened measurement portion 4a of oblong cross section is produced by thermoforming and is preferably made of a polyimide of the "Kapton" brand (having a density of 1.42 g/cm³ and a wall thickness of 25 μm±10%), which portion links together two cylindrical microtubes, for example made of LDPE (low-density polyethylene), having an internal diameter for example of about 1 mm. As illustrated in FIG. 3, the detection diodes 6a of the counting device 6 are arranged on either side of the external faces of the long sides 4aa of the portion 4a relative to its smallest transverse dimension, consisting here of its height h.

In this exemplary embodiment, the flattened portion 4a has an approximately rectangular cross section, the external faces of the short sides 4ab of which are curved with mutually symmetrical convex curvatures, and this portion has an [internal height h/internal width l] ratio of about 8%, where the internal height and the internal width are equal to 130 μm and 1490 μm respectively.

As regards the area ratio of the flow section of the flattened portion 4a—about 0.1937 mm²—to that of each adjacent cylindrical portion (with an internal cross section of about 0.785 mm²), this is slightly less than 25%.

Furthermore, the flattened portion 4a has a wall thickness e and a density d, the product e×d of which is approximately equal to 35.5 (with e=25 μm and d=1.42 g/cm³), this being very much less than the values normally used, which are generally between 150 and 200 in the case of the microlines made of LDPE (which have a lower density than that of "Kapton", but a substantially greater thickness), in such a way that the attenuation by this portion 4a according to the invention of the particles to be counted, such as electrons or positrons resulting from the beta-radioactivity, is considerably minimized.

As illustrated in FIG. 3, the flattened portion 4a is equipped, facing its large faces 4aa—which preferably are slightly convex—and overhanging its small faces 4ab, with two sets of said detection diodes 6a capable of counting said particles in each liquid microsample flowing therein (this overhang of the diodes 6a makes it possible to optimize their geometric acceptance, and therefore the "capture" of the particles to be counted).

The thermoforming process used to obtain this flattened portion 4a according to the invention comprises in particular the following steps:

- the portion 4a is placed, cold, in the forming mold;
- its two ends are connected to flexible microtubes for pressurization;
- pressure (1.5 bar of relative pressure) is applied;
- the mold is heated to 300° C. for 15 minutes;
- the mold is cooled under pressure; and
- the pressure is slowly lowered after cooling.

What is thus obtained by this thermoforming is a flattened counting portion 4a, the large faces 4aa of which each have an area of about 1.5 mm×35 mm, i.e. 52.5 mm², thereby minimizing the thickness of liquid that the positrons or electrons have to pass through in order to reach the detectors 6a.

Figure 4:
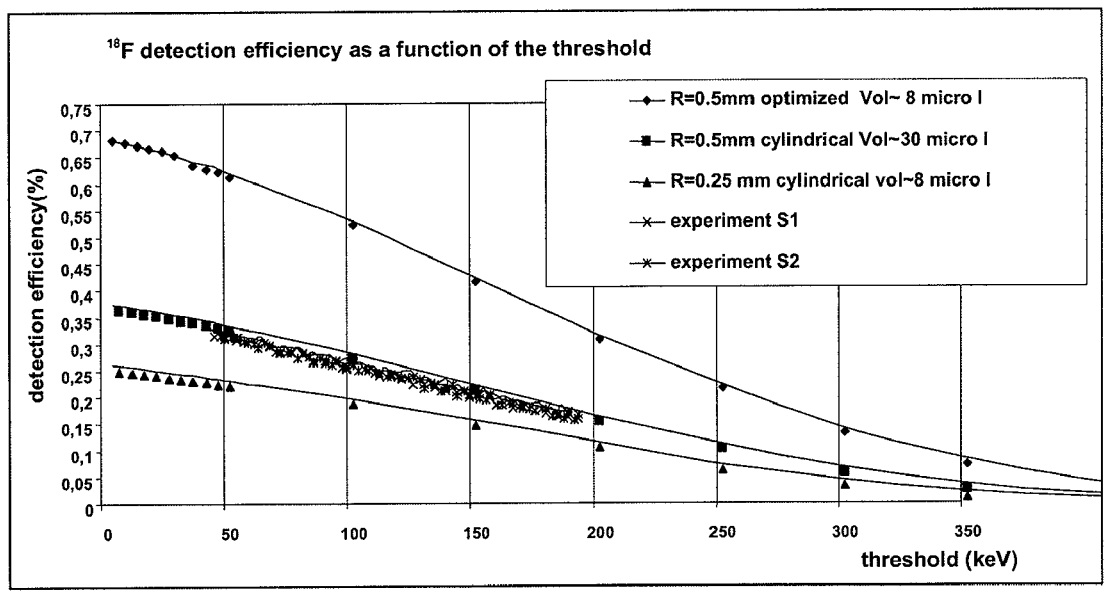
FIG. 4 is a graph illustrating the $^{18}F$-radiotracer detection efficiency as a function of the detection threshold, for three types of sampling lines that include this flattened counting portion according to the invention and, for comparative trials, two cylindrical microtubes.

The graph of FIG. 4 illustrates, in the form of simulation curves confirmed by experiment, the counting efficiency results obtained for two series of experiments S1 and S2, each carried out:

- with a line according to the invention of 0.5 mm radius for the cylindrical portions and incorporating this flattened portion 4a, with an 8 μl blood microsample volume taken (compatible with a mouse);
- with a first "control" line cylindrical over its entire length (i.e. with no flattened portion) having a radius of 0.5 mm and with a 30 μl blood microsample volume taken (compatible with a rat); and
- with a second "control" line cylindrical over its entire length (i.e. with no flattened portion) having a radius of 0.25 mm, with an 8 μl blood microsample volume taken.

Thanks to this flattened portion 4a, it may be noted that the positron detection efficiency increases, going from 32% with the cylindrical microtubes to more than 60% with the microtube of the invention, for the minimum threshold (approximately 46 keV). The gain is even greater as a cylindrical microtube line compatible with an 8 μl sample would give an efficiency of about 25%. The optimized microtube according to the invention thus makes it possible to work with 8 μl specimens, achieving more than 60% efficiency at the minimum threshold, compared with only 25% with a microtube entirely cylindrical over its length. This makes the sampling system 3 according to the invention particularly well suited for measuring the entry function of a mouse.

The device and the beta-particle counting method used in relation with the automated sampling system 3 will now be described in greater detail in relation to FIG. 1.

A few centimeters downstream of the first sampling line 4, each microsample passes as close as possible to the beta-particle counter 6, for which the wall thickness of the line causes only a very slight attenuation. The flattened portion 4a, fixed in the box 6b of the counter 6, makes it possible to minimize the amount of positron annihilation in the walls, and its geometry is such that it can contain the volume of a sample (either 30 μl or 8 μl) correctly centered beneath the six silicon detection diodes (measuring 10×10×0.3 mm$^3$) surrounding the portion 4a, as illustrated in FIG. 1. These diodes 6a are themselves surrounded by a lead shield 2 cm in thickness intended to eliminate the physical noise coming from the photons emanating from the animal 2. The rest of this measurement system 6 comprises an electronic processing/interfacing card, making the whole system compact and robust, being in the form of a box 6b of small dimensions (8×10×4 cm$^3$).

It is advantageous, in order to minimize the probability of annihilation in the blood of a positron coming from the beta-radioactivity, to give the flexible microtube the flattened shape of the portion 4a, at least at the point where it passes in front of the diodes 6a. Moreover, as explained above, this geometric configuration also ensures that the liquid is spread out as a thin sheet, thereby increasing the area of liquid facing the detecting surfaces. The configuration adopted for the measurement system 6 is as follows.

The flattened portion 4a, with a wall thickness of 25 μm, is sandwiched between the diodes 6a, with a thickness of 0.3 mm (three diodes 6a at the top and three others at the bottom).

The read-out electronics for these diodes 6a and the electronics controlling the data acquisition and transfer have been integrated into a single electronic module, which has been optimized so as to reduce as far as possible the electronic noise, allowing the detection threshold to be minimized for optimum efficiency.

The "front-end" electronics (shaper and discriminator) is provided by an ASIC (comprising 16 channels, a common threshold, 16 outputs+1 OR). The threshold is adjusted by the user. The acquisition card is a configurable USB test card benefiting from the flexibility of the USB interface of personal computers and from the progress made in FPGA (Field Programmable Gate Array) configurable digital circuits. This card allows a large number of signals to be rapidly processed and can be programmed from the interface of a computer.

The basic scheme is illustrated in FIG. 1. The sampling line 4 is extended by the flattened portion 4a, which takes over inside the box 6b, the blood emerging on the other side of the latter. This blood flow is performed by the peristaltic pump 7. The volume of the microsamples taken can be adjusted, as can their sampling times. These parameters are controlled by the computer of the control device 9 of the installation 1.

The minimum time between two microsamples being taken is 1 second. To cover the dynamic range of the kinetics of the radiotracer in the blood, the microsamples are taken every second after the injection for about 30 seconds to 1 minute, and then they are taken in more spaced apart time intervals, the slope of the curve being more gentle during this phase.

The connections between the various lines and the box 6b are designed to avoid any loss of volume of the microsamples and any diffusion between two adjacent microsamples being possible.

These blood microsamples are thus taken as discrete packets both in space and in time and they thus progress without diffusion as far as the sample treatment system 8 where they are stored and advantageously subjected to the extraction of at least one of their phases or of their components, for example by centrifugation.

It will be noted that this sampling system 3 according to the invention may advantageously be used in the field of preclinical research for the quantitative imaging of new tracers, especially in positron emission tomography (PET). In this case, the liquid in question is blood and the application consists in measuring the entry function for small animals, such as rats or mice. The small size of these animals, and therefore the small total amount of blood that they possess, limit the volume of each microsample to about 30 μl in the case of rats and about 8 μl in the case of mice.

Another possible application of the invention relates to a gaseous fluid consisting of air that has been labeled, for example by a xenon radioisotope. In this case, the device includes a counting portion 4a of oblong cross section which joins together two adjacent portions of this line having a larger flow section and which has an [internal height (h)/internal width (l)] ratio of 20%, in which the internal height and the internal width represent the smallest and largest transverse dimensions respectively of this portion, these being measured along two approximately perpendicular directions, said detection means extending transversely to this portion facing its entire internal width and on either side thereof.

The invention claimed is:

1. A device for counting elementary particles emitted by a fluid, the device comprising a line for transferring the fluid and, placed outside said line, counters for capturing and counting the elementary particles which are attenuated by a wall of said line and/or by the fluid before they reach said counter, the device including at least one counting portion of oblong cross section which joins together two adjacent portions of this line and which has an internal height (h)/internal width (l) ratio of 20% or less, in which the internal height and the internal width represent the smallest and largest transverse dimensions respectively of said counting portion, these being measured along two approximately perpendicular directions, said counters extending outside this portion transversely to said counting portion, facing its entire internal width and on either side thereof.

2. The device as claimed in claim 1, wherein said fluid is a liquid and wherein said counting portion has an internal height (h)/internal width (l) ratio of between 5% and 10%.

3. The device as claimed in claim 2, wherein said line is designed for the flow of liquid microsamples, said internal height (h) of the counting portion being between 100 μm and 250 μm and said internal width of this portion being greater than 1.3 mm, whereas the or each adjacent cylindrical portion has a diameter of between 0.8 mm and 1.2 mm.

4. The device as claimed in claim 3, wherein the area of the flow section of said counting portion is between 0.15 mm$^2$ and 0.25 mm$^2$ and wherein said portion has a length of between 30 mm and 40 mm so as to be able to contain a microsample of about 8 μl facing said counters.

5. The device as claimed in claim 1, wherein the ratio of the flow section of the counting portion to that of each adjacent portion is equal to or less than 35%.

6. The device as claimed in claim 5, wherein said internal height (h) of the counting portion is less than 20% of the internal diameter of each of the adjacent portions and wherein said internal width (l) of this portion is greater than 1.3 times this internal diameter.

7. The device as claimed in claim 1, wherein said counting portion has an approximately rectangular cross section, the long sides and/or the short sides of which are curved with mutually symmetrical curvatures, so that this portion has at least partly a substantially convex or concave external face.

8. The device as claimed in claim 1, wherein said counters comprise two sets of detectors placed respectively against or in the immediate vicinity of two approximately plane large faces of said counting portion, which faces are separated from each other by said height (h) and are joined together by two small faces of this portion, these sets of detectors overhanging said small faces in the direction of said width (l).

9. The device as claimed in claim 8, which is placed upstream of a computer-controlled peristaltic pump for sucking up, in bursts, a specified amount of samples to be taken, said large faces of said counting portion each having a slightly convex shape on their external side.

10. A method of counting elementary particles implemented by means of the device as claimed in claim 1, wherein a material that is substantially transparent at the wavelength of the particles emitted by said fluid is chosen for the wall of said counting portion.

11. The method as claimed in claim 10, characterized in that the particles are photons emitted by fluorescence.

12. The method as claimed in claim 10, wherein the particles are electrons or positrons emitted by beta-radioactivity, said wall having a thickness e, expressed in and a density d, expressed in $g/cm^3$, such that the product e×d is less than 100, so as to minimize the attenuation of these particles for the purpose of counting them.

13. The method as claimed in claim 12, wherein said counting portion is based on a thermoformed polymer with a density of 1.5 $g/cm^3$ or less, and wherein this portion has a wall thickness of less than 50 μm and preferably less than 30 μm.

14. The method as claimed in claim 12, wherein said fluid consists of blood microsamples that flow in said line, and in the plasma of said blood microsamples, a short-lived beta-radiotracer is diluted.

15. The method as claimed in claim 14, wherein said microsamples have been taken in succession from a mammal, such as a rat or a mouse, and each has a volume of less than 100 μl, the entire volume of each microsample being substantially located within said counting portion facing said counters, so that the microsamples follow one another in this portion as discrete packets both in space and in time.

16. A particle counting device for counting of elementary particles emitted by a fluid, the device comprising a line for transferring the fluid and, placed outside said line, detection means for detecting the particles, said particles being attenuated by a wall of said line and/or by the fluid, the device including at least one counting portion of oblong cross section which joins together two adjacent portions of said line having a larger flow section and which has an internal height (h)/internal width (l) ratio of 20% or less, in which the internal height and the internal width represent the smallest and largest transverse dimensions respectively of said counting portion, these being measured along two approximately perpendicular directions, said detection means extending transversely to said counting portion, facing its entire internal width and on either side thereof, and wherein said counting portion has a wall thickness e, expressed in μm, and a density d, expressed in $g/cm^3$, the product e×d of which is less than 100, in such a way that the attenuation by the counting portion of particles to be counted is minimized when these particles are electrons or positrons coming from beta-radioactive radiation emitted by said fluid.

17. The particle counting device as claimed in claim 16, wherein this product e×d is less than 50.

18. The particle counting device as claimed in claim 16, wherein said counting portion is based on a thermoformed polymer with a density of 1.5 $g/cm^3$ or less, and wherein this portion has a wall thickness of less than 50 μm.

\* \* \* \* \*

UNITED STATES PATENT AND TRADEMARK OFFICE
CERTIFICATE OF CORRECTION

| | | |
|---|---|---|
| PATENT NO. | : 7,821,248 B2 | Page 1 of 1 |
| APPLICATION NO. | : 11/963156 | |
| DATED | : October 26, 2010 | |
| INVENTOR(S) | : Reymond et al. | |

It is certified that error appears in the above-identified patent and that said Letters Patent is hereby corrected as shown below:

Column 9,

Line 27, "expressed in and" should read --expressed in μm, and--.

Signed and Sealed this
Twenty-eighth Day of June, 2011

David J. Kappos
*Director of the United States Patent and Trademark Office*